US00PP19671P2

(12) United States Plant Patent
Hooijman

(10) Patent No.: US PP19,671 P2
(45) Date of Patent: Feb. 3, 2009

(54) ROSE PLANT NAMED 'ESM ALANDALUZ'

(50) Latin Name: *Rosa hybrida*
Varietal Denomination: Esm Alandaluz

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 12/006,219

(22) Filed: Dec. 31, 2007

(51) Int. Cl.
*A01H 5/00* (2006.01)

(52) U.S. Cl. ..... Plt./136

(58) Field of Classification Search ..... Plt./136
See application file for complete search history.

(56) References Cited

PUBLICATIONS

UPOV–ROM GTITM Plant Variety Database 2008/01 GTI Jouve Retrieval Software, citation for Rose plant 'ESM ALANDALUZ'.*

* cited by examiner

*Primary Examiner*—Annette H Para
(74) *Attorney, Agent, or Firm*—C. A. Whealy

(57) ABSTRACT

A new and distinct cultivar of Rose plant named 'Esm Alandaluz', characterized by its long and upright flowering stems; uniform and freely flowering habit; salmon-colored flowers; and excellent postproduction longevity.

1 Drawing Sheet

Botanical designation: *Rosa hybrida.*
Cultivar denomination: 'ESM ALANDALUZ'.

BACKGROUND OF THE INVENTION

The present Invention relates to a new and distinct cultivar of Rose plant, botanically known as *Rosa hybrida,* commercially used as a cut flower Rose, and hereinafter referred to by the name 'Esm Alandaluz'.

The new Rose is a product of a planned breeding program conducted by the Inventor in El Quinche, Pichincha, Ecuador. The objective of the breeding program was to develop new freely-flowering cut flower Rose varieties with novel and attractive flower colors and excellent postproduction longevity.

The new cultivar originated from a cross-pollination made by the Inventor in February, 2002 of a proprietary Rose selection identified as code number 90, not patented, as the female, or seed, parent with a proprietary Rose selection identified as code number 91, not patented, as the male, or pollen, parent. The cultivar Esm Alandaluz was discovered and selected by the Inventor as a single flowering plant within the progeny of the stated cross-pollination in a controlled environment in El Quinche, Pichincha, Ecuador.

Asexual reproduction of the new Rose by cuttings at El Quinche, Pichincha, Ecuador since August, 2003, has shown that the unique features of this new Rose are stable and reproduced true to type in successive generations of asexual reproduction.

SUMMARY OF THE INVENTION

The following traits have been repeatedly observed and are determined to be the unique characteristics of 'Esm Alandaluz'. These characteristics in combination distinguish 'Esm Alandaluz' as a new and distinct cultivar:

1. Long and upright flowering stems.
2. Uniform and freely flowering habit.

3. Salmon-colored flowers.
4. Excellent postproduction longevity.

Plants of the new Rose differ from plants of the parent selections in the following characteristics:

1. Plants of the new Rose are more compact than plants of the parent selections.
2. Plants of the new Rose are not as freely flowering as plants of the parent selections.
3. Plants of the new Rose and the parent selections differ in flower color as plants of the parent selections have pink-colored flowers.

Plants of the new Rose can be compared to plants of the Rose cultivar Gracia, not patented. In side-by-side comparisons conducted in El Quinche, Pichincha, Ecuador, plants of the new Rose differed from plants of the cultivar Gracia in the following characteristics:

1. Plants of the new Rose had shorter flowering stems than plants of the cultivar Gracia.
2. Plants of the new Rose were narrower than plants of the cultivar Gracia.
3. Plants of the new Rose had larger flowers than plants of the cultivar Gracia.
4. Plants of the new Rose and the cultivar Gracia differed in flower color as plants of the cultivar Gracia had dark pink-colored flowers.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph at the bottom of the sheet comprises a side perspective view of a typical flowering stem of 'Esm Alandaluz'.

The photograph at the top left of the sheet is a close-up view of a typical flowering spray of 'Esm Alandaluz'.

The photographs at the top right of the sheet are close-up views of the upper and lower surfaces of typical leaves of 'Esm Alandaluz'.

DETAILED BOTANICAL DESCRIPTION

The new Rose has not been observed under all possible environmental conditions. The phenotype may vary somewhat with variations in environment such as temperature and light intensity, without, however, any variance in genotype. The aforementioned photographs, following observations and measurements describe plants grown in El Quinche, Pichincha, Ecuador, in a polyethylene-covered greenhouse and under commercial production practices. Plants were about 1.5 years old when the photographs and description were taken. During the production of the plants, day temperatures ranged from about 16° C. to 30° C., night temperatures ranged from about 12° C. to 16° C. and light levels ranged from about 800 to 1,200 foot-candles. In the following description, color references are made to The Royal Horticultural Society Colour Chart, 2001 Edition, except where general terms of ordinary dictionary significance are used.

Botanical classification:

*Rosa hybrida* cultivar Esm Alandaluz.

Parentage:

*Female, or seed, parent.*—Proprietary seedling selection of *Rosa hybrida* identified as code number 90, not patented.

*Male, or pollen, parent.*—Proprietary seedling selection of *Rosa hybrida* identified as code number 91, not patented.

Propagation:

*Type.*—By cuttings.

*Time to initiate roots.*—About seven to ten days at 26° C. to 30° C.

*Time to produce a rooted young plant.*—About four to five weeks at 22° C. to 26° C.

*Root description.*—Fibrous, thick; between N199B and N200A in color.

*Rooting habit.*—Freely branching; moderately dense.

Plant description:

*Plant form.*—Upright plant habit; long and upright flowering stems.

Growth habit. —Vigorous; freely basal branching habit; dense and bushy growth habit; about 14 to 15 flowering stems develop per year.

*Plant height.*—About 101 cm.

*Plant width (spread).*—About 50 cm.

*Lateral branches.*—Length: About 60 cm. Diameter: About 6 mm. Internode length: About 3.4 cm. Strength: Moderately strong. Texture: Smooth, glabrous. Color: Close to 144A. Thorns: Density: Moderate. Shape: Triangular with sharp acuminate apices. Height: About 3 mm to 5 mm. Diameter, at base: About 1 mm to 2 mm. Color, immature: Close to 145C. Color, mature: Close to 166C.

Foliage description:

*Arrangement.*—Alternate; compound with five leaflets per leaf.

*Leaf length.*—About 13 cm.

*Leaf width.*—About 9 cm.

*Leaflet shape.*—Ovate to oval.

*Leaflet apex.*—Cuspidate.

*Leaflet base.*—Attenuate.

*Leaflet margin.*—Serrate.

*Leaflet texture, upper and lower surfaces.*—Smooth, glabrous.

*Leaflet venation pattern.*—Pinnate.

*Leaflet color.*—Developing leaflets, upper surface: Close to 137A. Developing leaflets, lower surface: Close to 146B. Fully expanded leaflets, upper surface: Close to 139A; venation, close to 137C. Fully expanded leaflets, lower surface: Close to 147B; venation, close to 144A.

*Petioles.*—Length: About 1.5 cm. Diameter: About 6 mm. Texture, upper and lower surfaces: Smooth. Color, upper and lower surfaces: 146D; wings, 146A.

Flower description:

*Flower type and habit.*—Salmon-colored flowers with numerous petals. Consistently symmetrical rosette flowers. Freely and uniformly flowering; flowers arranged in terminal corymbs with about six open flowers and flower buds per corymb. Flowers persistent.

*Flowering season.*—Year-round under greenhouse conditions, optimal flowering from spring through autumn under garden conditions; flowering intermittent.

*Inflorescence height.*—About 22 cm.

*Inflorescence width.*—About 20 cm.

*Flower diameter.*—About 8.1 cm.

*Flower depth (height).*—About 3.2 cm.

*Flower longevity on plant.*—About 33 days.

*Flower longevity as a cut flower.*—About 11 days.

*Fragrance.*—Not detected.

*Flower buds (at stage of showing color).*—Shape: Ovoid. Length: About 3.4 cm. Diameter: About 2.2 cm. Color: Close to 144A.

*Petals.*—Quantity: Numerous; about 34 per flower. Length: About 3.5 cm. Width: About 3.8 cm. Shape: Broadly obovate to round. Apex: Rounded, cuspidate. Base: Attenuate. Margin: Entire. Texture, upper and lower surfaces: Smooth, glabrous. Color: When opening, upper surface: Close to 40C; towards the base, 150D; basal spot, 154B. When opening, lower surface: Close to 35B; towards the base, 154D. Fully opened, upper surface: Close to 44D; towards the base, 4C. Fully opened, lower surface: Close to 41D; towards the base, 4D.

*Sepals.*—Quantity per flower: Typically five. Length: About 3.1 cm. Width: About 1.1 cm. Shape: Deltoid. Apex: Tapered. Base: Truncate. Margin: Entire; ciliate. Texture, upper and lower surfaces: Pubescent; rugose. Color: When opening, upper surface: Close to 146D. When opening, lower surface: Close to 144A. Fully opened, upper surface: Between 145C and 143C. Fully opened, lower surface: Close to 144A.

*Peduncles.*—Strength: Strong; flexible. Aspect: Mostly erect. Length: About 2.9 cm. Diameter: About 4.6 mm. Texture: Smooth. Color: Close to 146A.

*Pedicels.*—Strength: Strong; flexible. Aspect: About 34° from vertical. Length: About 2.4 cm. Diameter: About 3.3 mm. Texture: Smooth. Color: Close to 144A.

*Reproductive organs.*—Stamens: Quantity: About 150 per flower. Anther length: About 2.7 mm. Anther shape: Reniform. Anther color: Close to 22A. Pollen amount: Moderate. Pollen color: N163C.

*Pistils.*—Quantity: About 121 per flower. Pistil length: About 1.2 cm. Stigma shape: Broadly reniform. Stigma color: Close to 153C. Style length: About 7.9 mm. Style color: Close to 155A. Ovary color: Close to 157C. Receptacle shape: Cup-shaped.

*Seeds/fruits.*—Seed and fruit development has not been observed on plants of the new Rose.

Pathogen/pest resistance: Plants of the new Rose have been observed to be resistant to *Botrytis*. Plants of the new Rose have not been observed to be resist to pests and other pathogens common to Roses.

Temperature tolerance: Plants of the new Rose have been observed to tolerate temperatures ranging from 0° C. to 35° C.

It is claimed:

1. A new and distinct Rose plant named 'Esm Alandaluz' as illustrated and described.

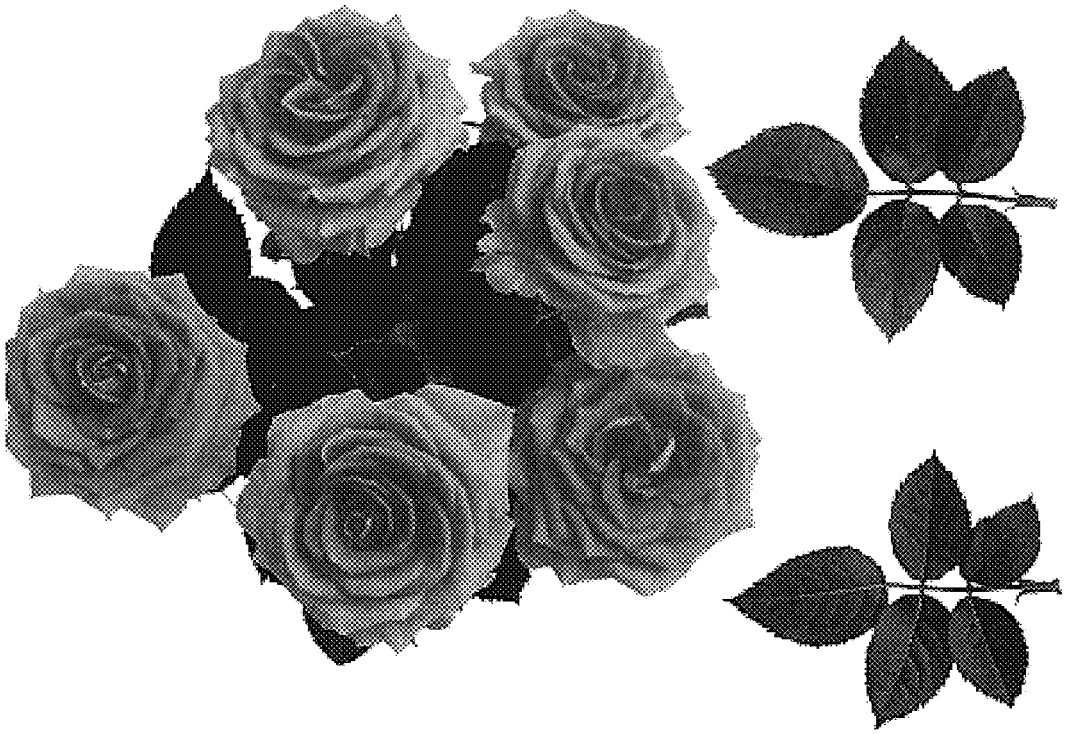
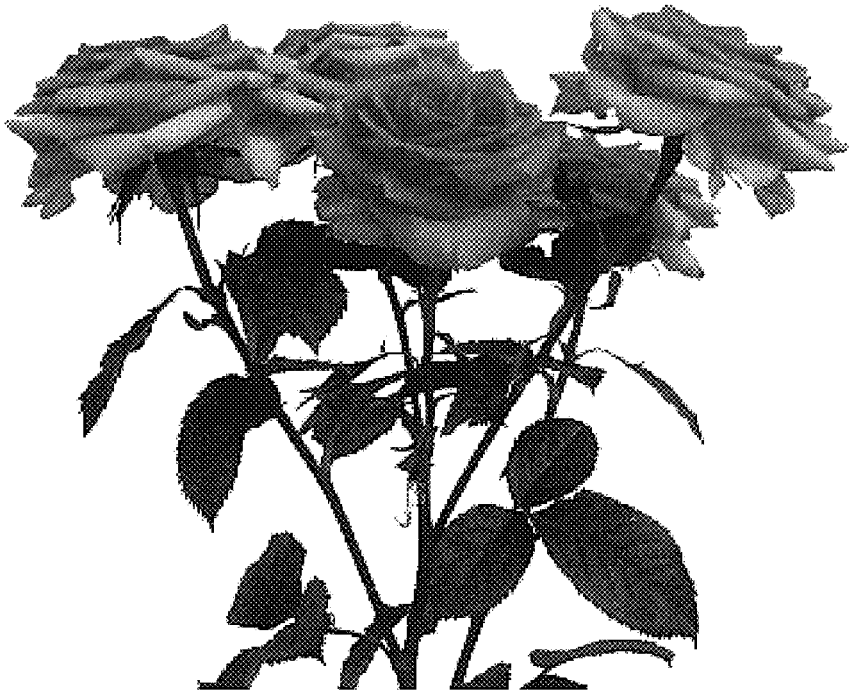

* * * * *